United States Patent
Guizzetti et al.

(10) Patent No.: US 12,245,679 B2
(45) Date of Patent: Mar. 11, 2025

(54) MAKE-UP PRODUCT

(71) Applicant: CHROMAVIS S.p.A., Offanengo (IT)

(72) Inventors: Giorgio Guizzetti, Vimercate (IT); Mauro Gaboardi, Pizzighettone (IT); Sergio Valvassori, Ripalta Cremasca (IT); Thibaut Fraisse, Offanengo (IT)

(73) Assignee: CHROMAVIS S.p.A., Offanengo (IT)

( * ) Notice: Subject to any disclaimer, the term of this patent is extended or adjusted under 35 U.S.C. 154(b) by 437 days.

(21) Appl. No.: 17/700,676

(22) Filed: Mar. 22, 2022

(65) Prior Publication Data

US 2022/0304450 A1     Sep. 29, 2022

(30) Foreign Application Priority Data

Mar. 26, 2021 (IT) .................. 102021000007529

(51) Int. Cl.
   *A61K 8/02*    (2006.01)
   *A45D 40/00*   (2006.01)
   *B44F 1/02*    (2006.01)

(52) U.S. Cl.
   CPC .............. *A45D 40/00* (2013.01); *A61K 8/02* (2013.01); *B44F 1/02* (2013.01); *A45D 2040/0012* (2013.01)

(58) Field of Classification Search
   CPC ..................................................... B44F 1/02
   See application file for complete search history.

(56) References Cited

U.S. PATENT DOCUMENTS

| 6,296,281 B1 * | 10/2001 | Stone ............... B42D 25/425 283/93 |
| 2005/0169858 A1 | 8/2005 | Look et al. |
| 2016/0030301 A1 * | 2/2016 | Baracat-Nasr ....... A61K 8/0216 264/328.1 |

(Continued)

FOREIGN PATENT DOCUMENTS

| EP | 3909561 A1 | 11/2021 |
| JP | 2011173294 A | 9/2011 |
| WO | 2019199037 A1 | 10/2019 |

OTHER PUBLICATIONS

Christine, "Guerlain Sun in the City Collection for Spring/Summer 2012", 2012, p. 1-7, https://www.temptalia.com/guerlain-sun-in-the-city-collection-for-springsummer-2012/.*

*Primary Examiner* — Humera N. Sheikh
*Assistant Examiner* — Julia L Rummel
(74) *Attorney, Agent, or Firm* — Dickinson Wright PLLC; Andrew D. Dorisio

(57) ABSTRACT

A make-up product (1) comprising a transfer or writing surface (2), at least one part (3) of said transfer surface (2) having a surface finish featuring parallel grooves (S), so as to determine a plurality of relief elements (P), each with at least a first face (A) and a second face (B) facing the exposed surface of the said part (3) of the transfer surface (2), each first face (A) facing in an essentially opposite direction to each second face (B), at least some of the first faces (A) having cavities (20) or reliefs arranged so as to form a first FIG. 4), at least some of the second faces (B) having cavities (20) or reliefs so as to form a second FIG. 5) so that, when tilting the make-up product (1) so that mostly the first faces are visible (A), the first FIG. 4) is visible, while when tilting the make-up product (1) so that mostly the second faces are visible (B), the second figure is visible (5).

9 Claims, 5 Drawing Sheets

(56) References Cited

U.S. PATENT DOCUMENTS

2016/0066595 A1* 3/2016 Grolimund ............... B44F 1/02
                                                      426/104
2019/0030946 A1  1/2019 Zhang

* cited by examiner

MAKE-UP PRODUCT

This application claims priority to Italian Patent Application for Invention No. 102021000007529 filed on Mar. 26, 2021.

FIELD OF THE INVENTION

The present invention relates to a make-up product.

BACKGROUND ART

As it is known, make-up products are aimed at an exacting public. Without detracting from the intrinsic quality of the make-up product, the aesthetic factor of the part which transfers the make-up product plays a fundamental role in the end-user's choice thereof.

SUMMARY OF THE INVENTION

The object of the present invention is to provide a make-up product with an attractive, innovative appearance.

This and other objects are achieved by means of a make-up product according to the technical teachings of the claims annexed hereto.

BRIEF DESCRIPTION OF THE FIGURES

Further features and advantages of the innovation will become clearer in the description of a preferred but not exclusive embodiment of the product, illustrated—by way of a non-limiting example—in the drawings annexed hereto, in which.

DETAILED DESCRIPTION OF THE INVENTION

With reference to the figures stated, reference number 1 is used to denote, as a whole, a make-up product.

Figure 1:
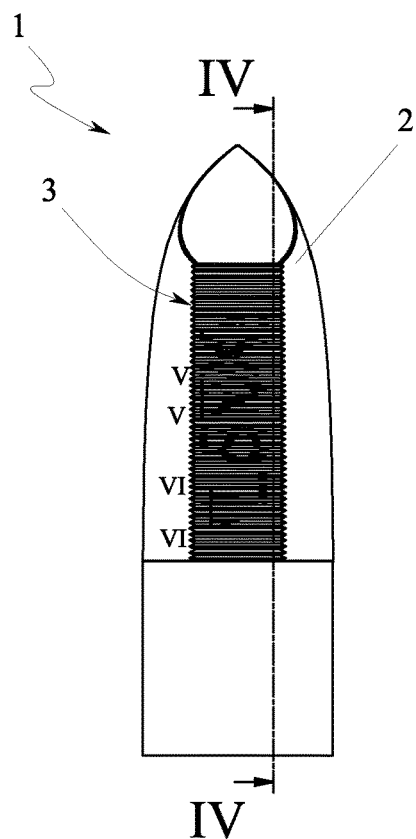
FIG. 1 is a plan view of a make-up product according to the present invention.

The make-up product shown in FIG. 1 is the transferring part of a lipstick or stick for lips. But it may also be any other kind of make-up product such as foundation, eye make-up, or any product in a solid state (such as compact, baked, or poured powders).

As mentioned above, the make-up product 1 comprises a transfer surface 2, also referred to as a 'writing surface'.

In this document, the term 'transfer surface' means a surface which—if touched or applied to a body part for make-up purposes—transfers part of the constituent substance thereof thereto.

Therefore, within this context, a make-up product as a lip gloss, has a transfer surface even though the product is not coloured.

Instead, if the make up product is for example a lipstick, the transfer surface also transfers its colour to the skin of the user.

Basically the 'transfer surface' (or writing surface) is that surface of the make-up product that may be used or may be put in contact with the skin of the user to perform a make-up operation.

At least a part 3 of the said transfer surface 2 has a surface finish featuring parallel grooves S.

The grooves may have any cross-section, such as a polygonal cross-section or a curved cross-section.

If the cross-section is polygonal, the grooves are preferably triangular.

Some possible shapes that the grooves may have are shown in FIGS. 8A to 8F.

The grooves S may run in a straight line from a plan view. But other conformations are also possible, for example curved, wavy, zigzag conformations etc.

In this document, reference will be made to grooves S running in a straight line with a triangular cross-section.

As can be seen from the figures, the grooves in this embodiment run along a straight line when seen from a plan view. Even if the grooves were slightly curved they would run in a straight line when seen from a plan view, since the machining may be performed in the cylindrical surface (for example of a lipstick) with grooves running around the circumference.

The grooves S determine a plurality of relief elements P on the surface.

In the embodiment described, the said elements P are prismatic, with a triangular base, preferably featuring an equilateral or isosceles triangle.

Furthermore, all the prismatic elements P of the make-up product in FIG. 1 are arranged so that each one is touching the next, without interruption.

Figure 4:
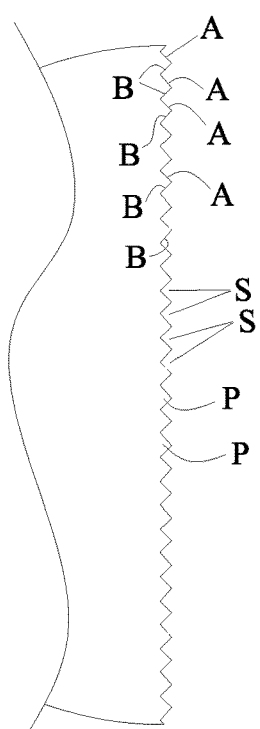
FIG. 4 is a simplified section view taken along line IV-IV in FIG. 1.
Figure 8:
FIG. 8 is a section view taken along line VIII-VIII in FIG. 7.
Figure 9:
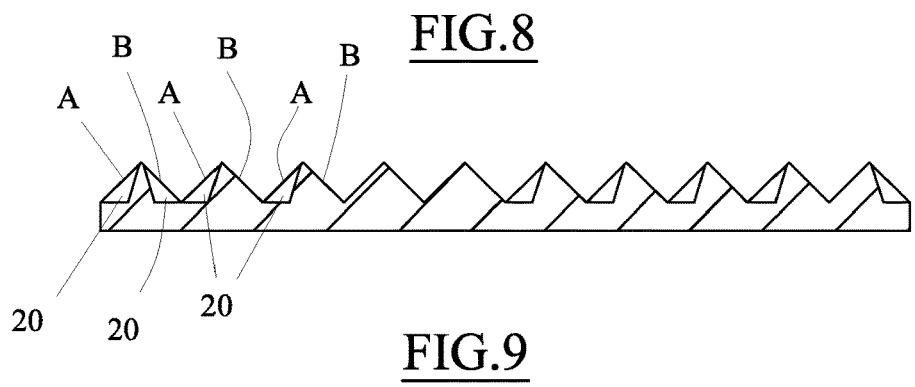
FIG. 9 is a section view taken along line IX-IX in FIG. 7.

These features of the prismatic elements P are clearly visible in FIG. 4 or in FIG. 8.

It is understood that differently shaped grooves can determine different prismatic elements P, such as, for example, those shown in FIGS. 8A to 8F as stated above.

In any case, the prismatic elements P each have at least a first face A and a second face B facing the exposed surface of the said part 3 of the transfer surface.

Each first face A faces in essentially the opposite direction to each second face B.

Figure 5:
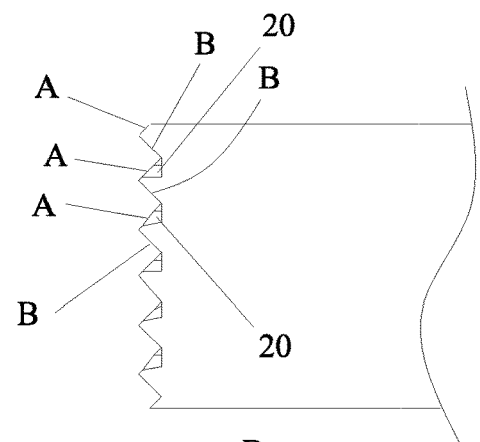
FIG. 5 is a simplified section view taken along line V-V in FIG. 1.
Figure 6:
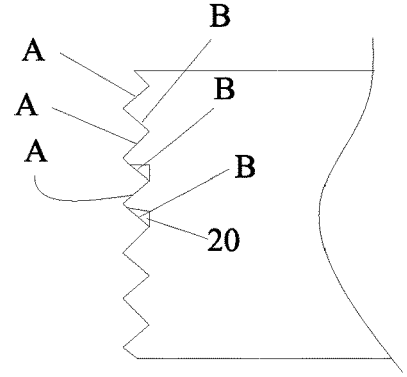
FIG. 6 is a simplified section view taken along line VI-VI in FIG. 1.

Furthermore, at least some of the first faces A have cavities 20 (or reliefs) arranged so as to form, overall, a first FIG. 4, while at least some of the second faces B have cavities 20 or reliefs so as to form, overall, a second FIG. 5.

Figure 2:
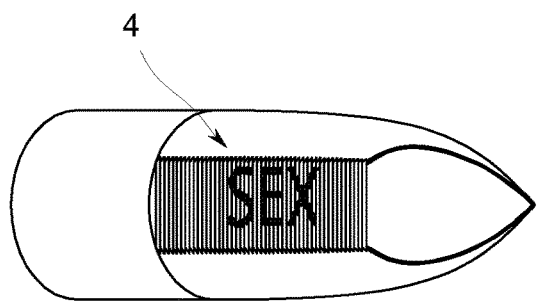
FIG. 2 is a perspective view of the make-up product in FIG. 1 from a first angle.
Figure 3:
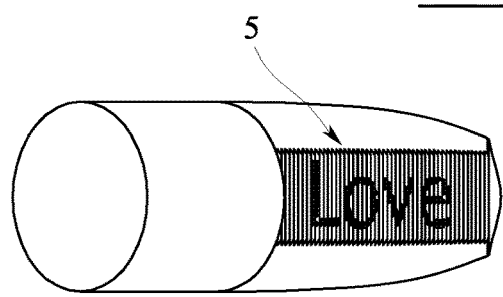
FIG. 3 is a perspective view of the make-up product in FIG. 1 from a second angle.

In this way, as can be easily deduced from the comparative analysis of FIG. 2 and FIG. 3, by tilting the make-up product 1 so that mostly the first faces A are visible (FIG. 2), the first FIG. 4 is visible, i.e., in the example shown, the word 'SEX'. Meanwhile, by tilting the make-up product 1 so that mostly the second faces B are visible (FIG. 3), the second FIG. 5 is visible, i.e. the word 'LOVE'.

In the case described, the first FIG. 4 and second FIG. 5 are essential written words, but in this document, the term 'figure' means any kind of graphics, design, logo, or alpha-numerical combinations, with any font and style, etc.

Figure 11:
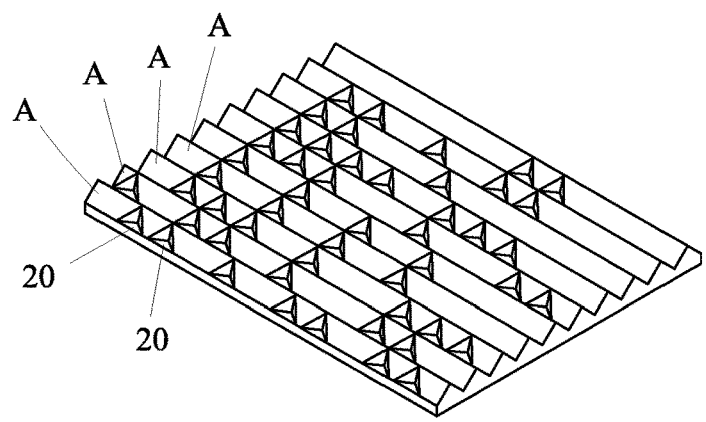
FIG. 11 and FIG. 12 are a perspective view of the surface in FIG. 7 from, respectively, a first and a second angle.
Figure 12:
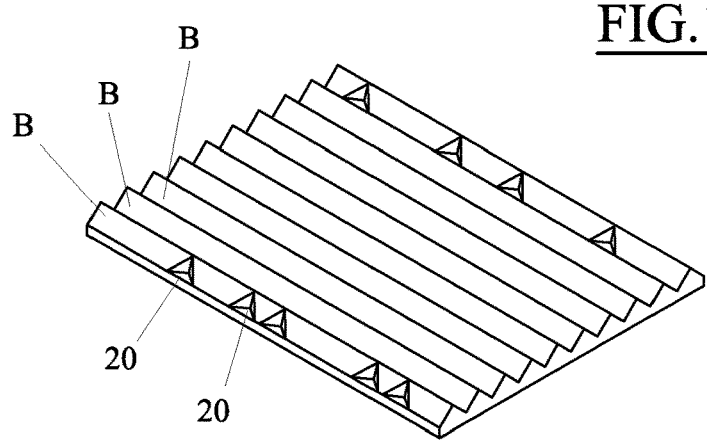
Figure 8A:
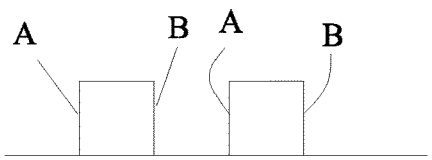
FIGS. 8A to 8F are schematic examples of possible textures of the product in FIG. 1.
Figure 8B:
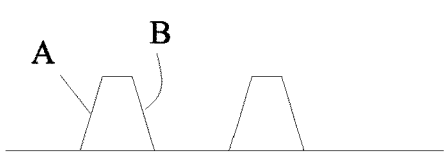
Figure 8C:
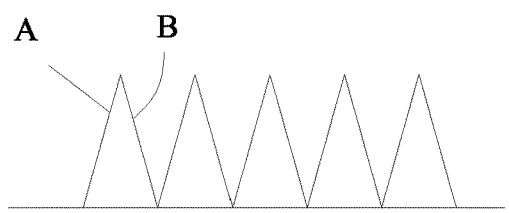
Figure 8D:
Figure 8E:
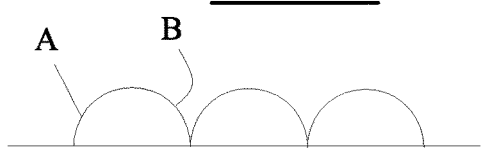
Figure 8F:
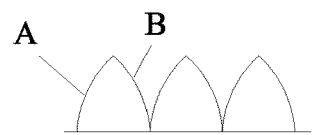
Figure 13:
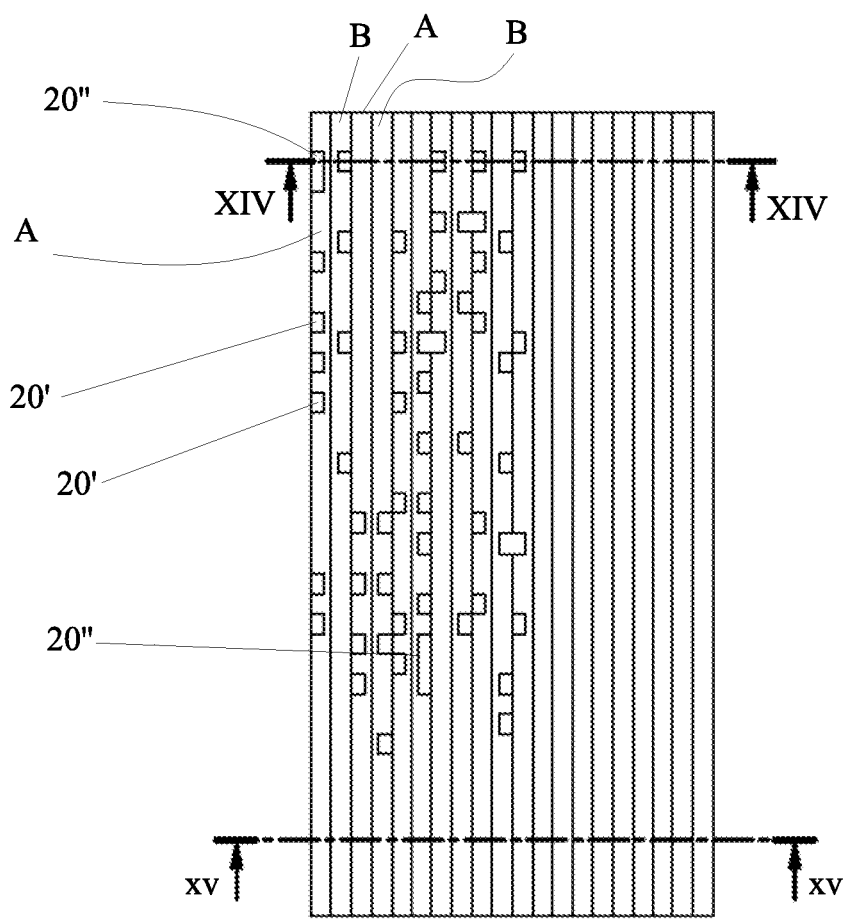
FIG. 13 is a plan view of a possible different embodiment of the part shown in FIG. 7.
Figure 14:
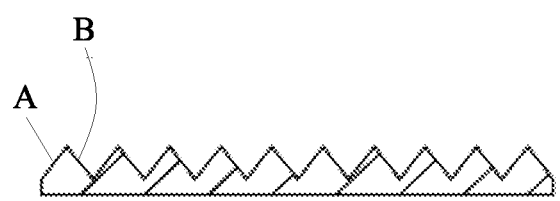
FIGS. 14 and 15 are, respectively, simplified section views taken along lines XIV-XIV and XV-XV in FIG. 13.
Figure 15:
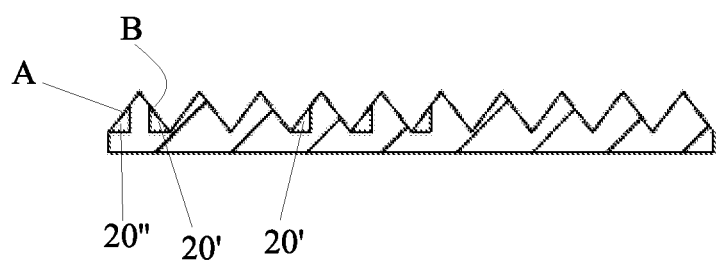

A three-dimensional example of the effect obtainable is shown in FIGS. 11 and 12, which have more detail than FIGS. 2 and 3, even though the words SEX and LOVE are not visible completely because part 7 is shown in great detail.

Figure 7:
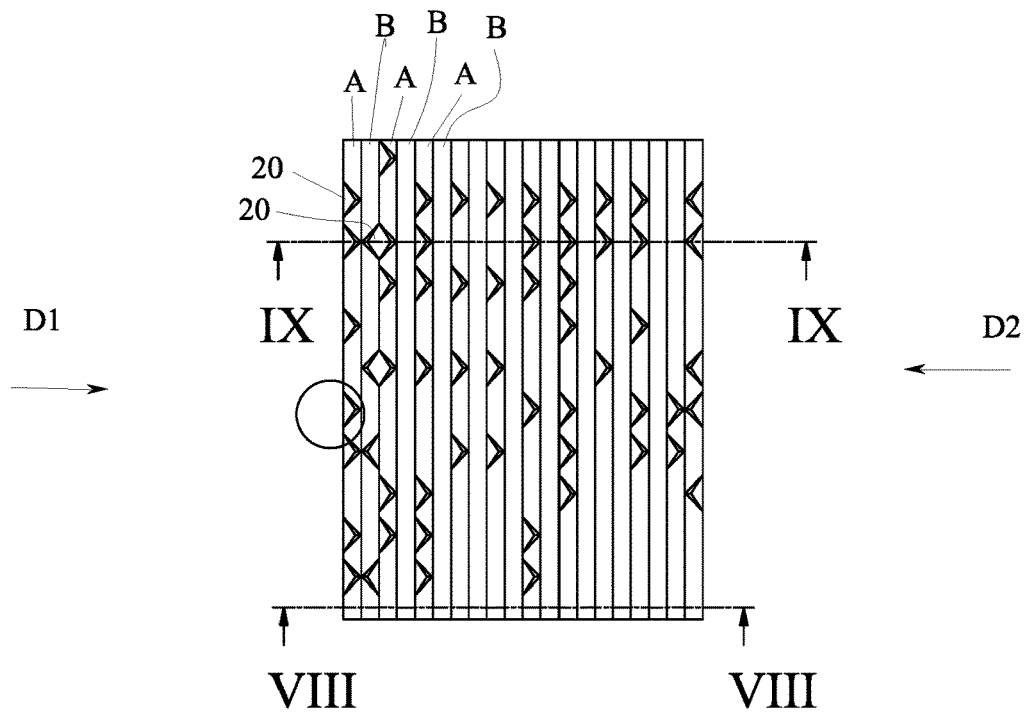
FIG. 7 is a partial plan view of a part of a 'transfer surface' of the product in FIG. 1.

If you look at the portion shown in FIG. 7 in the direction shown by the arrow D1, you see that which is shown in FIG. 11, i.e. only the cavities 20 in the second faces B, i.e. part of the word 'LOVE'. If, on the other hand, you look at the same portion in the direction shown by the arrow D2, you see that which is shown in FIG. 12, or only the cavities present on the first faces A, i.e. part of the word 'SEX'.

With the system described, the appearance of the surface changes depending on the position from which a user looks at it.

The cavities 20 may be essentially dot-like.

In this document, the term 'dot-like' does not mean that they must be circular in shape, rather they may be square or any other shape, just like the pixels on a monitor.

Figure 10:
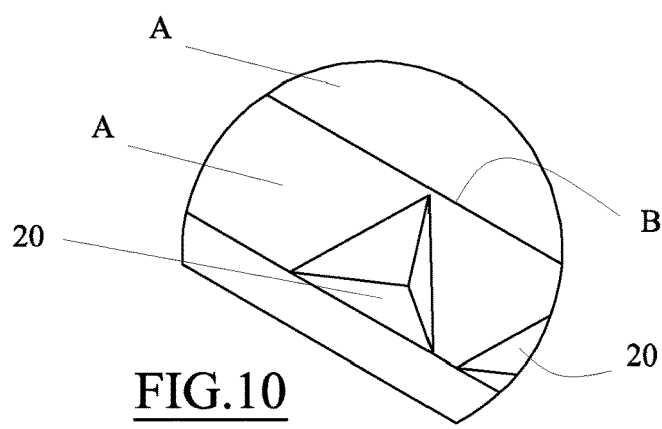
FIG. 10 is a detailed view of the part circled in FIG. 7.

Advantageously, the cavities 20 have a concave pyramidal surface with a triangular base, preferably with the base of the pyramid exposed on the surface. In this regard, see the detail in FIG. 10.

Figure 16:
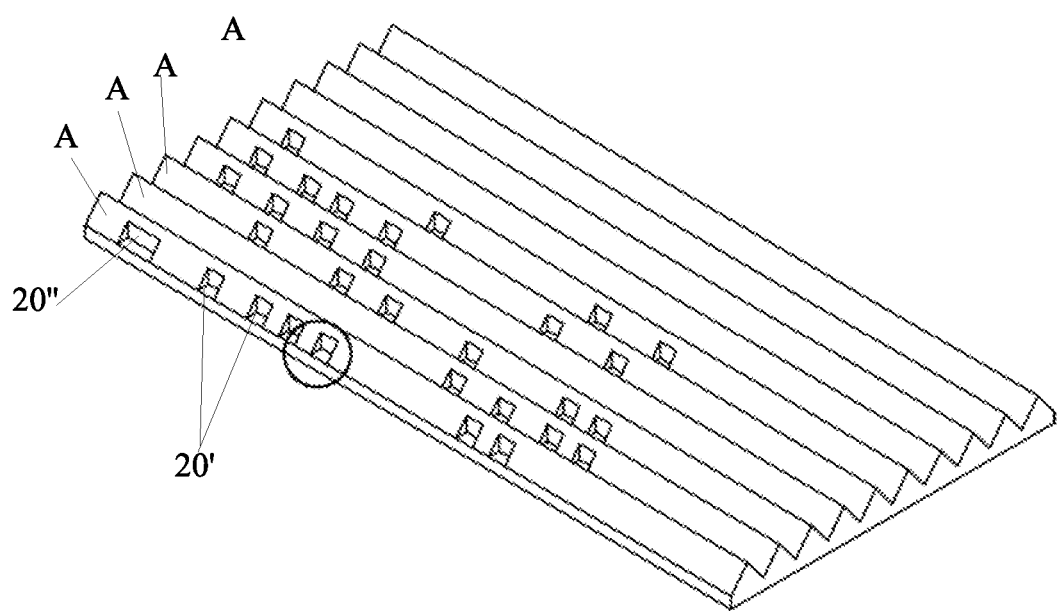
FIG. 16 is a perspective view of the part shown in FIG. 13 from a first angle.
Figure 17:
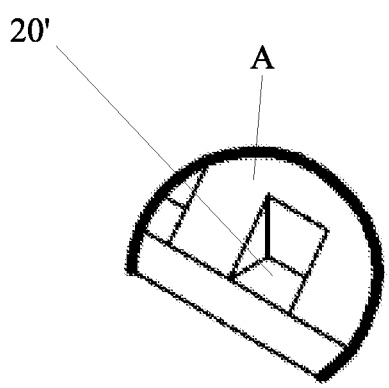
FIG. 17 is an enlarged view of the part circled in FIG. 16.

Another possible conformation of the cavities 20' is a triangular prism with one face exposed on the surface, like the one shown in FIGS. 13-16, and more specifically in FIG. 17.

The cavities may also have a non-dot-like conformation, and may be oblong, for example, such as the one denoted 20" shown on the far left, on the first prismatic element, in FIG. 16. In the case shown, the cavities 20" may have an oblong triangular prism with one face exposed on the surface.

Obviously, it is possible that some cavities (or reliefs) can have a dot-like conformation while others, also on the same face of the prismatic elements, have an oblong conformation, just as in FIG. 11. This depends on the final effect you wish to achieve.

The concept is to essentially have a series of long wedges (prismatic elements) which are preferably parallel and have a triangular cross-section. On a series of parallel oblique faces of the wedges, incisions are made (i.e. the cavities or reliefs) which may be prismatic, curved, or any shape that can cause the light to be reflected in such a way as to create a shaded area, where you wish, causing a word or image to appear.

The cross-section of the wedges considered is triangular, but there is nothing to prevent it having a cross-section formed of two curves or with another shape. What matters is the creation of two series of faces (with a linear or curved cross-section) that are opposite one another so that they can be machined as described above.

In the series of mutually opposing faces, engravings (or reliefs) are created with the same concept of creating a shaded area that can cause the desired second word or image to appear.

Various embodiments of the innovation have been disclosed herein, but further embodiments may also be conceived using the same innovative concept.

The invention claimed is:

1. Make-up product (1) comprising:
    a transfer surface (2), at least a part (3) of said transfer surface (2) having a surface finish with parallel grooves (S), so as to define a plurality of elements (P) in relief, each with at least a first planar face (A) and a second planar face (B), each of the elements (P) facing a free surface of said part (3) of the transfer surface,
    wherein each first planar face (A) faces in a first direction, and wherein each of the second planar face (B) faces in a second direction different from the first direction;
    wherein at least some of the first planar faces (A) present cavities (20) or reliefs arranged so as to form a first figure (4), and wherein at least some of the second planar faces (B) present cavities (20) or reliefs so as to form a second figure (5) so that,
        by tilting the make-up product (1) in a first tilted position so that the first planar faces (A) are visible and facing toward a viewer and the second planar faces are facing away from the viewer the first figure (4) is visible and the second figure (5) is not visible, and
        by tilting the make-up product (1) in a second tilted position so that the second planar faces (B) are visible and facing toward the viewer and the first planar faces are facing away from the viewer, the second figure (5) is visible and the first figure (4) is not visible.

2. Make-up product (1) according to claim 1, wherein the parallel grooves(S) have a polygonal section.

3. Make-up product (1) according to claim 1, wherein said polygonal section of the parallel grooves(S) is triangular.

4. Make-up product (1) according to claim 1, in which the parallel grooves(S) extend in straight lines, when seen in plan view.

5. Make-up product (1) according to claim 1, wherein said elements (P) are prismatic, with a triangular base.

6. Make-up product (1) according to claim 5, in which at least some prismatic elements (P) are mutually resting side by side, without interruption.

7. Product according to the claim 1 wherein the cavities (20) have a pyramidal concave surface with a triangular base.

8. Make-up product (1) according to claim 1, in which the cavities (20") are oblong, and/or shaped like a triangular prism with one face exposed on the surface.

9. Make-up product (1) according to claim 1, wherein said first (4) and/or said second figure (5) is a writing.

* * * * *